US010163181B2

(12) United States Patent
Dominick et al.

(10) Patent No.: US 10,163,181 B2
(45) Date of Patent: Dec. 25, 2018

(54) METHOD AND SYSTEM FOR JOINT EVALUATION OF A MEDICAL IMAGE DATASET

(71) Applicants: Lutz Dominick, Eggolsheim (DE); Vladyslav Ukis, Nürnberg (DE)

(72) Inventors: Lutz Dominick, Eggolsheim (DE); Vladyslav Ukis, Nürnberg (DE)

(73) Assignee: Siemens Aktiengesellschaft, Munich ( * ) Notice: Subject to any disclaimer, the term of this patent is extended or adjusted under 35 U.S.C. 154(b) by 365 days.

(21) Appl. No.: 14/973,202

(22) Filed: Dec. 17, 2015

(65) Prior Publication Data

US 2016/0180492 A1 Jun. 23, 2016

(30) Foreign Application Priority Data

Dec. 17, 2014 (EP) .................................... 14198598

(51) Int. Cl.
*G06T 1/20* (2006.01)
*G16H 40/63* (2018.01)
*G16H 80/00* (2018.01)
*G06T 5/20* (2006.01)
*G06T 7/00* (2017.01)
*G06T 11/60* (2006.01)
*G06F 19/00* (2018.01)

(52) U.S. Cl.
CPC ................ *G06T 1/20* (2013.01); *G06F 19/00* (2013.01); *G06T 5/20* (2013.01); *G06T 7/0012* (2013.01); *G06T 11/60* (2013.01); *G16H 40/63* (2018.01); *G16H 80/00* (2018.01); *G06T 2200/24* (2013.01)

(58) Field of Classification Search
CPC combination set(s) only.
See application file for complete search history.

(56) References Cited

U.S. PATENT DOCUMENTS 5,187,790 A * 2/1993 East ........................ G06F 9/468 718/107
2006/0235936 A1 10/2006 Lei et al.
2008/0085040 A1 * 4/2008 Basu ..................... G06T 11/005 382/128

(Continued)

OTHER PUBLICATIONS

European Search Report for related European Application No. 14198598.6, dated May 29, 2015 with English Translation.

*Primary Examiner* — Shyue Jiunn Hwa
(74) *Attorney, Agent, or Firm* — Lempia Summerfield Katz LLC

(57) ABSTRACT

For effective joint evaluation of a medical image dataset on a first data processing device and at least one second data processing device that is connected to the first data processing device via a data transmission network, a first application is performed in the first data processing device, and a second application is performed in the second data processing device. Each of the applications has a respective graphical user interface having at least one segment for display of a view of the image dataset. An image processing pipeline is associated with each segment for deriving the view from the image dataset. Partially processed data of the image dataset is decoupled from the image processing pipeline of the segment of the first application, is transferred to the second application, and there is coupled to the image processing pipeline of the segment of the second application for preparing the view.

13 Claims, 6 Drawing Sheets

Legend

| | | | | | | | |
|---|---|---|---|---|---|---|---|
| 1 | System | 6 | Input unit | 11 | LAN | 16 | (Central) collaboration unit |
| 2 | Device | 7 | Assessment station | 12 | Wireless network | 17 | (Public) cloud |
| 3 | (Data transmission) network | 8 | PC workstation | 13 | Internet | 18 | Memory |
| 4 | Processor | 9 | Tablet | 14 | Firewall | B | Image dataset |
| 5 | Visual display unit | 10 | Smartphone | 15 | Application | V | View |

(56) References Cited

U.S. PATENT DOCUMENTS

| | | | | |
|---|---|---|---|---|
| 2011/0126127 | A1* | 5/2011 | Mariotti | G06F 19/321 715/753 |
| 2012/0307116 | A1* | 12/2012 | Lansel | H04N 9/045 348/273 |
| 2014/0282624 | A1* | 9/2014 | Holt | G06F 9/542 719/318 |

* cited by examiner

Legend

| | | | | | | | | | |
|---|---|---|---|---|---|---|---|---|---|
| 1 | System | 6 | Input unit | 11 | LAN | 16 | (Central) collaboration unit |
| 2 | Device | 7 | Assessment station | 12 | Wireless network | 17 | (Public) cloud |
| 3 | (Data transmission) network | 8 | PC workstation | 13 | Internet | 18 | Memory |
| 4 | Processor | 9 | Tablet | 14 | Firewall | B | Image dataset |
| 5 | Visual display unit | 10 | Smartphone | 15 | Application | V | View |

Legend

| | | | |
|---|---|---|---|
| 15, 15a, 15b | Application | 27 | Assessment management module |
| 20 | GUI | V | View |
| 21 | Segment | P | Parameter |
| 22 | Front end | E | Event |
| 23 | Back end | I | Input |
| 24 | (Image processing) pipeline | F | Assessment |
| 26 | Event handler | | |

Legend

| | | | |
|---|---|---|---|
| 15, 15a, 15b | Application | V | View |
| 24 | (Image processing) pipeline | P | Parameter |
| 25 | Filter | E | Event |
| 26 | Event handler | I | Input |
| 27 | Assessment management module | F | Assessment |
| B | Image dataset | T1-T4 | Partially processed data |

Legend

| | | | | | |
|---|---|---|---|---|---|
| 15, 15a, 15b | Application | 27 | Assessment management module | 42 | Collaboration pilot |
| 16 | (Central) collaboration unit | 30 | Presenter pipeline | V | View |
| 20 | GUI | 31 | Presenter segment | P | Parameter |
| 21 | Segment | 32 | Observer pipeline | E | Event |
| 22 | Front end | 33 | Observer segment | I | Input |
| 23 | Back end | 36 | Mark | F | Assessment |
| 24 | (Image processing) pipeline | 37 | Mark | T3 | Partially processed data |
| 26 | Event handler | | | | |

FIG 5

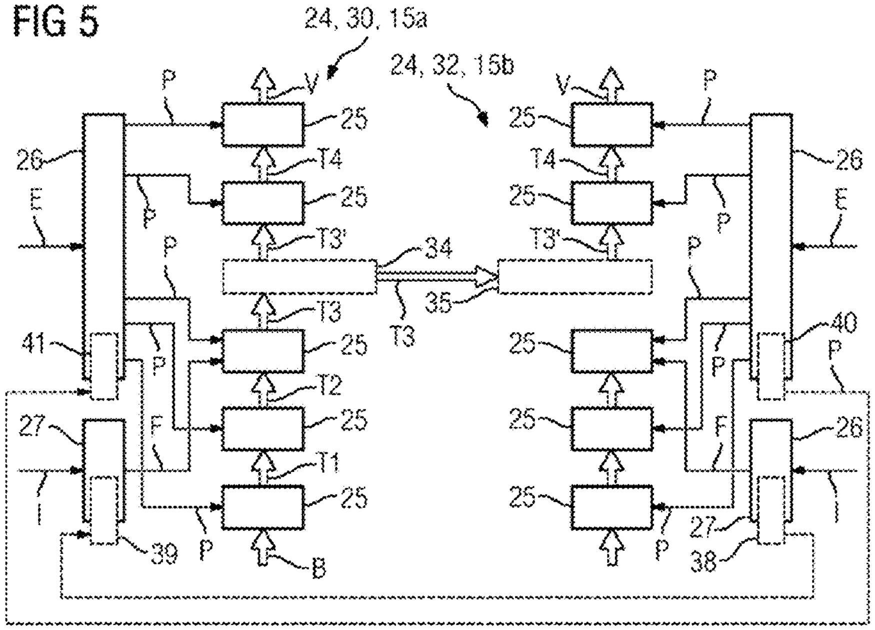

Legend

| | | | | | |
|---|---|---|---|---|---|
| 15, 15a, 15b | Application | 35 | Coupling filter | I | Input |
| 24 | (Image processing) pipeline | 38 | Withdrawable module | F | Assessment |
| 25 | Filter | 39 | Withdrawable module | B | Image dataset |
| 26 | Event handler | 40 | Withdrawable module | T1-T4 | Partially processed data |
| 27 | Assessment management module | 41 | Withdrawable module | T3' | Partially processed data |
| 30 | Presenter pipeline | V | View | | |
| 32 | Observer pipeline | P | Parameter | | |
| 34 | Coupling filter | E | Event | | |

Legend

| | | | | | |
|---|---|---|---|---|---|
| 2 | Device | 50 | (Local) collaboration unit | 55 | Data exchange manager |
| 15 | Application | 51 | Presentation channel | 56 | Audio channel |
| 16 | (Central) collaboration unit | 52 | Presentation manager | 57 | Audio manager |
| 17 | (Public) cloud | 53 | Event channel | B | Image dataset |
| 18 | Memory | 54 | Event manager | | |

METHOD AND SYSTEM FOR JOINT EVALUATION OF A MEDICAL IMAGE DATASET

This application claims the benefit of EP 14198598.6, filed on Dec. 17, 2014, which is hereby incorporated by reference in its entirety.

BACKGROUND

The present embodiments relate to joint evaluation of a medical image dataset on at least two data processing devices that are connected via a data transmission network, a corresponding system.

In medicine, increasing use is made of collaborative processing work, in which digital medical image datasets are jointly evaluated (e.g., assessed) by a plurality of users (e.g., medical experts from the same specialist field or different specialist fields within medicine). In modern medicine, this assessment is normally carried out electronically, using data processing equipment (e.g., computers).

For the purpose of a high degree of working efficiency and a high-quality assessment result, it is usually useful for the evaluation to take place at the same time for all the users concerned (e.g., in the context of a discussion in which the users may exchange information directly and in real time). Typically, the experts concerned therefore gather in front of a screen for joint evaluation of an image dataset. However, it is frequently not possible or at least not good value for money to gather the users concerned at one location at the same time. Rather, it is often desirable to carry out the joint evaluation of medical image datasets remotely, using a plurality of data processing devices that are connected via a data transmission network.

Experience has shown that it is of great importance for the efficiency of a collaborative evaluation process of this kind that the same information is made available to all the experts concerned without substantial loss of time. For example, it is to be provided that all those concerned see the same image information. This requirement is not usually satisfactorily realizable using data processing systems and methods of the prior art.

The prior art enables a plurality of users to see and assess the same dataset on respective local data processing devices simultaneously, using respective local applications at the same time independently of one another. However, the assessments respectively generated by the individual operators are not then visible, or only visible with a considerable time delay, to the respectively other users, with the result that an effective exchange of information is not possible. When the same image dataset is processed independently by a plurality of users, there is a high risk that the work results of one user will be overwritten by the actions of another user and will thus be lost.

One of the users may make his or her screen content (e.g., the information displayed on his or her screen) available to another data processing device by using remote screen technology. However, distribution of the screen display using remote screen technology may entail considerable loss of quality of the image data to be displayed (e.g., if the data processing devices concerned have screens or other visual display units with different form factors). For this reason, usually only the user who is carrying out distribution can and may generate assessments in the system, which in turn counteracts effective collaboration. Similar problems also occur with conventional applications for online conferences or webinars.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and an associated system that efficiently support joint evaluation of a medical image dataset on a plurality of data processing devices connected via a data transmission network are provided.

The image datasets that are evaluated in the course of the method or by the system may optionally be single images with two-dimensional image information, image stacks having a plurality of in each case two-dimensional individual images (e.g., layers), three-dimensional image data (e.g., volumes), or moving image sequences with two-dimensional or three-dimensional image information. For example, within the scope of one or more of the present embodiments, the system is configured to support the evaluation of image datasets of various kinds.

One or more of the present embodiments take as a starting point a data processing system having at least two data processing devices that are connected via a data transmission network for the mutual exchange of data. The term "data processing device" (e.g., device) may be a processor (e.g., computer) equipped with visual display units and input units. At least one of the devices may in this case be a personal computer or a workstation that is equipped with one or more screens as visual display units and with keyboard, mouse etc. as input units. As an alternative or in addition, at least one of the devices is formed by a notebook, tablet, personal digital assistant (PDA) or smartphone. In principle, in some embodiments, the system may contain only devices of the same type. Usually, however, the system will include any combination of devices of various kinds, as desired. For example, in an exemplary embodiment, the system includes as the devices a personal computer and a tablet.

The data transmission network is, for example, a local area network (LAN) that includes wired and/or wireless data transmission circuits. Within the scope of one or more of the present embodiments, however, the data transmission network may also be composed of a plurality of subnetworks based on like or different data transmission standards (e.g., two LANs connected over the Internet).

The devices used within the scope of the method are in this case configured for evaluation of medical image datasets in that in each of these devices at least one application (e.g., software application) that has a graphical user interface (GUI) having at least one segment for displaying a view of a medical image dataset is implemented.

The term "view" may designate a digital, two-dimensional image that has been derived from an underlying medical image dataset and may be displayed directly on the screen.

If the underlying image dataset has an item of two-dimensional image information, such as in the case of a simple X-ray image, then the view derived therefrom is, for example, an extract of this image information that has been compressed (e.g., in terms of pixel resolution), rotated, re-colored, smoothed (e.g., denoised) and/or processed in some other way.

If the underlying image dataset, for example, in the case of a conventional computer tomograph, is an image stack (e.g., a plurality of layers of in each case two-dimensional image information), the view derived therefrom typically reproduces a processed (as described above) extract of a particular layer of this image stack. As an alternative, the view may also be derived from a combination (e.g., an additive or subtractive overlaying) of a plurality of layers.

If the underlying image dataset includes 3D image data (e.g., volumes), then the view derived therefrom represents, for example, a section through the three-dimensional image information of the image dataset or an image scene generated by volume rendering.

The term "segment" designates a software module that, within the context of the GUI, serves to display the view on a screen or on the other visual display units of the device. Within the GUI, the segment typically takes the form of a frame or window inside which the view is displayed. In this case, the segment typically contains a number of tools (e.g., software tools), such as drop-down menus, by which a user interacting with the GUI may bring about actions for manipulating the image data being displayed. Within the scope of one or more of the present embodiments, the GUI of each application may contain one or more of these segments. For example, at least one of the applications is set up such that, by user interaction with the GUI, any number of segments as desired may be reversibly opened and closed again.

For deriving the view to be displayed in the segment from the underlying image dataset, an image processing pipeline is associated with each segment. The term "image processing pipeline" (e.g., pipeline) generally designates a software structure having a plurality of filters connected one after the other. Each filter performs a particular processing step on the data of the image dataset. Accordingly, the term filter designates a software module that contains, as the input variable, original data or data of the image dataset that has been partially processed (e.g., by a filter upstream, where appropriate) and outputs further processed data of the image dataset to the segment for display, or where appropriate, to a filter downstream for further processing.

Examples of the filters of the pipeline are, for example, an xy filter for centering an image extract to be displayed, in relation to an image plane of the underlying image dataset, a zoom filter for enlarging or reducing the image extract that is to be displayed as a view, a color filter for re-coloring the image information (e.g., color filter may cover anatomical filters, such as bone filters or soft tissue filters, that eliminate from the image information, or highlight therein, particular color value ranges of the image information corresponding, as is known from experience, to particular anatomical structures such as soft tissue or bone), and a rotary filter that rotates the image information about a predetermined angle within the image plane.

Filters of the types described above (e.g., color filters) may also be represented a plurality of times within the pipeline. A plurality of the functions described above (e.g., xy centering and zoom) may be combined in one filter.

In one embodiment, the pipeline takes a form such that during the running time of the application individual filters of the pipeline may be brought into the pipeline, automatically or by user interaction with the GUI, or may be removed from the pipeline.

Thus, as a result of the pipeline, the view created from the underlying image data is generated in a multi-stage process, in that the image data runs through the filters that are connected one after the other and in so doing is successively further processed.

In the course of the method according to one or more of the present embodiment, within the system described above, a first application is performed in a first device, and a second application is performed in a second device. During this, partially processed data from the image dataset to be evaluated is decoupled from the pipeline (e.g., image processing pipeline) of the segment (or, where applicable, of one of a plurality of segments) of the first application and is transferred to the second application. The associated segment of the first application is designated the "presenter segment" below. The image processing pipeline of this presenter segment from which the partially processed data is decoupled is accordingly designated a "presenter pipeline" below.

The decoupled data is received by the second application and at the second application is coupled to the image processing pipeline of the segment there (or, where applicable, of one of a plurality of segments of the second application) for preparing the view. The relevant segment of the second application is also designated the "observer segment" below. The image processing pipeline of the observer segment to which the partially processed data is coupled is designated the "observer pipeline".

The decoupling and coupling process described above is performed in that, in the course of the multi-stage processing process that is carried out by the presenter pipeline, a copy of the partially processed data is generated and is processed further in the observer pipeline (e.g., where appropriate, instead of other data that was processed there hitherto) to give the view displayed in the observer segment.

The partially processed data is also processed further in the presenter pipeline to generate the view to be displayed in the presenter segment.

The multi-stage processing process for generating the views for the presenter segment and the observer segment is carried out in a first section in a single channel in the presenter pipeline and is then split into a first processing branch and a second processing branch. The first processing branch continues in the presenter pipeline and results in generation of the view for the presenter segment. The second processing branch passes through the observer pipeline and results in generation of the view for the observer segment.

As a result of this coupling of the presenter pipeline to the observer pipeline, it is possible in a simple manner to provide that the same image information is made available to different users who are working at different devices remotely from one another, in that certain image manipulation steps are carried out only once, in the first section of the presenter pipeline. The branching processing structure offers sufficient flexibility to generate the view to be generated in a manner that accords with the technical restrictions of the respective device.

In this way, in one embodiment, the partially processed data of the image dataset is decoupled from the presenter pipeline, for example, before undergoing adjustment of the form factor (e.g., at the presenter end) of this data, and is also coupled to the observer pipeline before undergoing adjustment of the form factor (e.g., at the observer end).

In this context, the term "form factor" designates an item of information that characterizes the image resolution of the screen or the other visual display units of the respective device. The form factor includes, for example, specifications of the line and column length of the display (e.g., the number of pixels displayed respectively horizontally and vertically)

and, optionally, a specification of the color resolution that may be displayed for each pixel. Additionally and as an alternative to this, however, the form factor may also be specified in a different way (e.g., by specifying the length-to-height ratio of the image (in the form of the specification "4:3") and/or by specifying the length of the screen diagonal, etc.).

In this context, the term "adjustment of the form factor" designates a processing step by which previously processed data of an image dataset is adjusted to the individual form factor of a particular device. Thus, for example, the image data for a view intended to be displayed on a smartphone or a tablet normally is to be relatively highly compressed (e.g., the pixel resolution is scaled down) in the course of form factor adjustment. Form factor adjustment may include a plurality of processing steps.

In one embodiment, all the processing steps relating to form factor adjustment of the data of the image dataset are performed after the partially processed data is decoupled from the presenter pipeline. Thus, the form factor adjustment is performed separately for the presenter pipeline and the observer pipeline, respectively. All the processing steps of medical relevance (e.g., selection of the image extract to be displayed) and optional steps such as re-coloring, smoothing, color selection, etc. are by contrast performed in the presentation pipeline before decoupling of the partially processed data.

Further data of other data types (e.g., non-image data) is associated with the actual image data of the image dataset in a manner that is conventional per se. This non-image data includes, for example, metadata that contains information on the patient, the time of capture, the imaging modality used for capture, and the capture parameters used. During generation of the view, the metadata may be shown as an inset on the actual image data, and is completely or partly in the form of image text (e.g., image information reproducing alphanumeric information content). Typically, for this, a text field is generated in a corner region of the view by the image processing pipeline and reproduces a selection of the metadata associated with the image dataset. The text field is inset on top of the actual image information.

In addition or as an alternative, the non-image data includes assessments that are generated during the process of evaluating the image dataset by user interaction with the GUI of an application. Typically, the one or each assessment includes one or more markings, such as a circle, arrow, etc. and a descriptive text generated by the user. Conventionally, these assessments, unlike the metadata, are not stored directly in the image dataset but in a separate file that is linked by data processing to the image dataset. When the view is generated, the assessments are overlaid on the actual image information, similarly to the metadata.

In the course of the method according to one or more of the present embodiments, the image data of the image dataset and the non-image data (e.g., the data of the at least one further type of data such as metadata and/or assessments) are decoupled from the presenter pipeline separately from one another (e.g., before being overlaid) and are transferred to the second application. Similarly, the image data and the non-image data are coupled to the observer pipeline separately from one another and are always combined to form the view (e.g., are overlaid) only at this location.

Separately, transferring image data and metadata and/or assessments makes it possible, in a simple and effective manner, to present the non-image data in a manner that is always legible on different devices having different form factors. The present method differs in this respect from a pure remote screen function in which the alphanumeric constituents of the view are enlarged and reduced in the same way as the image data and are thus frequently illegible.

In an advantageous embodiment, it is provided for, in the observer segment, to generate assessments on the view displayed there. According to the method, an assessment of this kind, generated at the observer end, is transferred from the associated second application to the first application and there is fed into the presenter pipeline.

As mentioned above, the GUI of the first application and/or that of the second application optionally include a plurality of segments of the type described above. According to the method, one of these segments may be selectable as the presenter segment by user interaction with the GUI. As a result of this selection, partially processed data of the image dataset is decoupled from the associated image processing pipeline in the manner described above and is transferred to the second application.

As an alternative or in addition hereto, the GUI of the second application is set up such that by user interaction with the GUI, at least one of the segments there may be selected as the observer segment.

In one embodiment, the GUI of the first application or the second application is in this case structured such that each of the segments there may be selected as a presenter segment or an observer segment. Optionally there may be the limitation that only a single segment may be selected as the presenter segment and only a single segment may be selected as the observer segment at a given moment. In one embodiment, the selection of a segment as the presenter segment or as the observer segment is reversible, so it is possible by user interaction with the respective GUI to cancel this again.

In one embodiment, the GUI of at least one application is structured such that both at least one presenter segment and at least one observer segment are formed therein or may be selected by user interaction with the GUI as a presenter segment and an observer segment, respectively. For example, the user interface in this case may be structured such that each of the segments there may be selected by user interaction with the user interface optionally as a presenter segment or an observer segment. In the course of the method according to one or more of the present embodiments, an application of this kind may thus be operated both as a "first application" and as a "second application" in the sense of the statements above.

According to one or more of the present embodiments, the system described above is set up for performing the method described above. In the context of the system, the first application is thus set up to decouple partially processed data of the image dataset from the pipeline (e.g., presenter pipeline) of the associated segment (e.g., presenter segment) and to transfer the partially processed data to the second application. Similarly, the second application is set up to receive the transferred, partially processed data of the image dataset and, for the purpose of preparing the view, to couple the transferred, partially processed data to the pipeline (e.g., observer pipeline) of the associated segment (e.g., observer segment).

The advantageous embodiments of the method that are described above are accordingly in each case optionally implemented as functional features of the system.

Thus, the first application may be set up to decouple the image data of the image dataset and the associated non-image data from the presenter pipeline separately from one another. Similarly, the second application is in this context set up to couple the image data and the non-image data to the observer pipeline separately from one another and there to combine the image data and the non-image data to give the view.

The first application may be set up to decouple the partially processed data of the image dataset from the presenter pipeline before this data has undergone form factor adjustment and also to couple the partially processed data to the observer pipeline before the data undergoes form factor adjustment.

In an advantageous embodiment, the second application is set up such that, by user interaction with the associated GUI in the observer segment, an assessment may be generated and may be transferred to the first application. In this context, the first application is set up to feed this assessment into the presenter pipeline before the partially processed data is decoupled.

In one embodiment, the system includes, in addition to the first application and the at least one second application, a central collaboration unit that brings about the data transfer described above between these applications. This central collaboration unit is in this case implemented in a cloud (e.g., a public cloud).

The term "cloud" (e.g., processor cloud) may be a data processing device that is provided and operated by a cloud vendor that is independent of the user. In this case, the cloud vendor provides the user with the hardware and, where appropriate, the software of the cloud as a service, within the scope of a contract of use (e.g., subscription).

Depending on the user circle relevant for the respective cloud, a distinction is made between a "public cloud," the services of which are available to anyone, and a "private cloud" that is only accessible to users of a certain organization (e.g., a certain corporation).

For every user of a public cloud, the access rights to certain hardware and software constituents of the cloud are regulated by the subscription awarded to the user. Consequently, public clouds are, for example, "multi-tenant" arrangements. This designates the capability of keeping data, user management, and processor operations for users holding different subscriptions strictly separate. Thus, a user of the public cloud cannot see the data, user management, or processor operations of a different user holding a different subscription.

In a development, the applications, as in a conventional conference environment, are also set up for mutual transfer of sound signals (e.g., captured speech) and optionally video signals. The transfer of sound and video may in this case also be brought about by way of the central collaboration unit.

The advantages associated with the present embodiments consist, for example, in the fact that operation of the system by the method requires only a relatively small amount of data transmission, particularly since only the already partially processed image data and, where appropriate, non-image data such as metadata and/or assessments are transferred between applications but not whole image datasets. Thus, for example, any but negligible latency periods for data transmission are effectively avoided. Corresponding image information may be displayed on a plurality of devices at a quality that is in each case optimized with respect to the technical requirements of the respective device.

A crucial advantage of the system and the method is that different applications may display substantially the same views of the image dataset even if the image manipulation functions required to generate these views are not available in all the cooperating applications. Rather, it is sufficient if the required functions are present in the presenter pipeline. In this way, it is possible, for example, for views of mammogram datasets that have been prepared using data manipulation algorithms in the presenter pipeline that are specific to mammography also to be displayed in observer segments of other applications that do not themselves have these algorithms available. The use of the method and the associated system is also particularly advantageous for planning and performing emergency treatments with support from imaging investigative methods (e.g., computer tomography), particularly since in such cases it is frequently not possible, for time reasons, to assemble the procedure team required for evaluating the image data at the location of the procedure.

BRIEF DESCRIPTION OF THE DRAWINGS

Exemplary embodiments of the invention will be explained in more detail below with reference to the drawings, in which:

FIG. 5 shows, in an illustration according to FIG. 3, the image processing pipelines of the two applications in the collaborative operation.

Mutually corresponding parts, variables and structures are provided with the same reference numerals in all the figures below.

DETAILED DESCRIPTION

Figure 1:
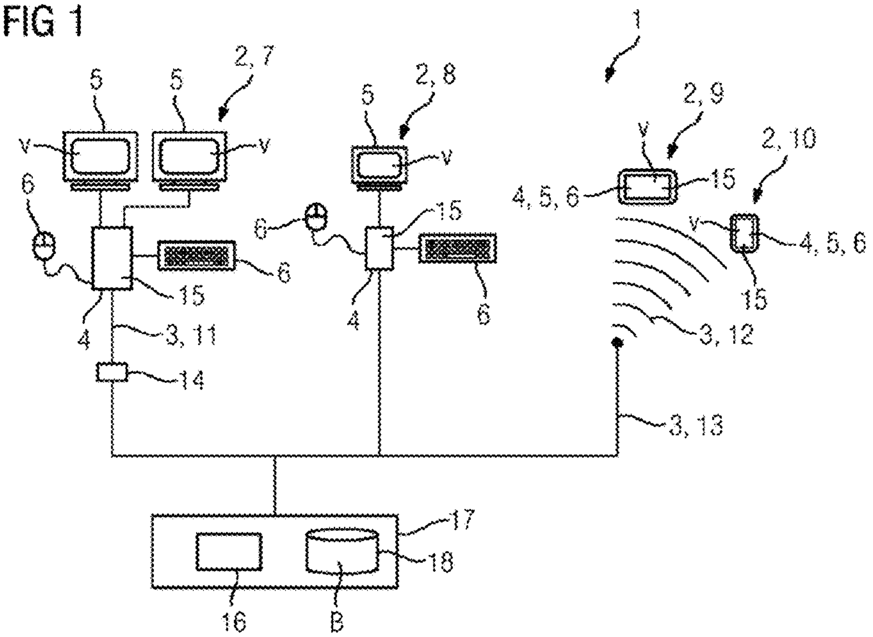
FIG. 1 shows, in a schematic block diagram, one embodiment of a system for joint evaluation of a medical image dataset by a plurality of users.

FIG. 1 shows, greatly simplified and in schematic form, a system 1 for joint evaluation of medical image datasets B.

As regards hardware, the system 1 includes a plurality of data processing devices (e.g., devices 2) that are connected to one another for mutual data exchange via a network 3 (e.g., a data transmission network).

Each device 2 includes, for example, a processor 4 having connected visual display units 5 (e.g., one or more screens) and input units 6 for user interaction with the respective device 2 (e.g., a keyboard or a computer mouse).

In the example according to FIG. 1, four different devices 2 are illustrated by way of example. The four devices 2 include: an assessment station 7, in which the processor 4 is formed, for example, by a powerful workstation, and which includes as visual display units 5 two large-format screens; a PC workstation 8, in which the processor 4 is formed by a conventional desktop personal computer (PC) and the visual display units 5 are formed by a conventional computer monitor; a tablet 9, in which the processor 4, the visual display units 5 and the input units 6 are integrated in a portable compact unit with touch display; and a smartphone 10, in which the processor 4, the visual display units 5, and the input units 6 are also integrated in a portable compact unit (e.g., of smaller format than the tablet 9) with touch display.

As an alternative or in addition to the devices 2 illustrated, the system 1 may also include data processing devices of other types, such as one or more notebooks. Within the scope of one or more of the present embodiments, the system 1 may include any number of devices 2, but at least two devices 2.

The devices 2 may be arranged spatially separated from one another in the operational condition of the system 1. Any arrangement of devices 2 distributed worldwide may be provided. For example, the assessment station 7 forms a constituent of an IT infrastructure of a medical facility (e.g., a clinic), while the PC workstation 8 is a home workstation in a private premises of the user, and the tablet 9 and the smartphone 10 are mobile units operated at varying locations.

In accordance with the respective spatial arrangement of the devices 2, the network 3 includes, in one embodiment of the system 1, a single, unified network or a plurality of cooperating subnetworks. In the simplified example according to FIG. 1, the subnetworks of the network 3 include, for example, a wired LAN 11 of the medical facility in which the assessment station 7 is arranged, a wireless network 12 (e.g., a WLAN or a mobile telephone network) by which the tablet 9 and the smartphone 10 are linked to the system 1, and the Internet 13, by which the other subnetworks are connected to one another.

Local subnetworks such as the LAN 11 are in this case typically connected to the Internet 13 by a firewall 14, which is indicated by way of example.

As regards software, the system 1 includes a number of applications 15 (e.g., software applications) for displaying and processing the image datasets B. In each case, at least one of the applications 15 is implemented ready to run in each of the devices 2. In principle, in this context, the same applications 15 may be implemented in all the devices 2. In one embodiment of the system 1, however, different applications 15 or different variants of an application 15 that each have a range of functions adapted to a specific medical area of application and/or to the respectively associated device 2 are implemented on the individual devices 2.

For example, the application 15 implemented in the assessment station 7 is formed by a full version of a specialized application for displaying and assessing mammogram images, while in the PC workstation 8, for example, a version of the same application 15 that is limited in scope, from which numerically complex functions of the full version are omitted, is implemented. By contrast, in the tablet 9 and the smartphone 10, the applications 15 implemented are, for example, only generic display programs for image data (e.g., multi-modality readers) with no specialized functions for image processing and image evaluation.

In addition to the applications 15, the system 1 includes, as regards software, a central collaboration unit 16 that coordinates cooperation between the individual applications 15. In one embodiment of the system 1, the collaboration unit 16 is implemented in a cloud 17 (e.g., a public cloud; the "Azure" cloud service from Microsoft). The cloud 17 is, in this arrangement, not part of the system 1 in a strict sense but rather is only utilized by the system 1.

Further, the system 1 includes a memory 18 in which the image datasets B are stored. In the example according to FIG. 1, the memory 18 is also arranged in the cloud 17. In principle, the image datasets B may additionally or as an alternative also be stored at the location of one of the devices 2 (e.g., in the medical facility in which the assessment station 7 is arranged). The memory 18 may, for example, also include a plurality of individual memories that are arranged in one location or distributed across a plurality of locations. For example, image datasets B of different types are stored in the memory 18 (e.g., single images (image datasets B having only two-dimensional image information, image stacks and volumes)). Purely for reasons of simplification, it will be assumed below that the image dataset B to be evaluated is a single image (e.g., a mammograph record).

Figure 2:
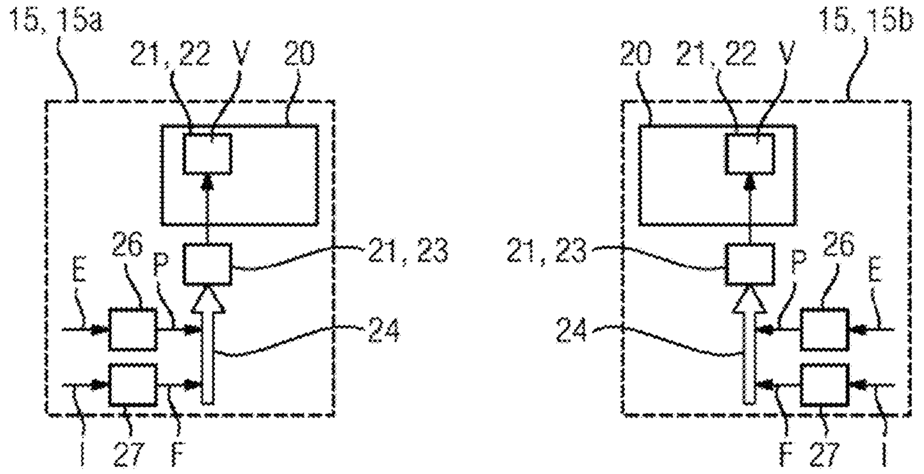
FIG. 2 shows, in a schematic block diagram, one embodiment of two applications.

FIG. 2 shows, diagrammatically and greatly simplified, the structure of two applications 15*a* and 15*b* that may be any of the applications 15 shown in conjunction with FIG. 1.

As shown in FIG. 1, each of the two applications 15*a*, 15*b* includes a graphical user interface (GUI) 20. As a constituent of the GUI 20, each of the applications 15*a*, 15*b* includes one or more segments 21, each of which serves to display a respective view V of the dataset B to be evaluated, and of which only one is illustrated in each case explicitly in FIG. 2, purely for reasons of clarity.

In the GUI 20, each segment 21 takes the form of a rectangular frame or window in which the view V is displayed. Here, each segment 21 contains a number of drop-down menus that the user may activate by interaction with the GUI 20 (e.g., by clicking on a corresponding button with the mouse or a comparable input unit, or by performing a particular mouse pointer movement). By way of these drop-down menus, the user may, by interaction with the GUI 20, bring about actions for manipulating the displayed image data.

The number of segments 20 positioned next to one another in the GUI 20 is in this case determined in user-specific manner. For this purpose, the user may open and close any desired number of segments 21 by interaction with the GUI 20.

In an exemplary embodiment of the application 15 in a client-server environment, for technical reasons each segment 21 may be formed by a front end 22 and a back end 23, where the front end 22 defines the graphical operating elements of the segment 21 (e.g., the image plane and the drop-down menus), while the back end 23 contains the program logic that is linked to these operating elements. In an alternative embodiment, as implemented, for example, in the tablet 9 and the smartphone 10, the functionality of the front end 22 and the back end 23 is grouped into a single software component.

For each segment 21, the applications 15*a*, 15*b* contain a respective associated pipeline 24 (e.g., image processing pipeline) that serves for deriving, from the underlying image dataset B, the view V that is to be presented in the respective segment 21.

Figure 3:
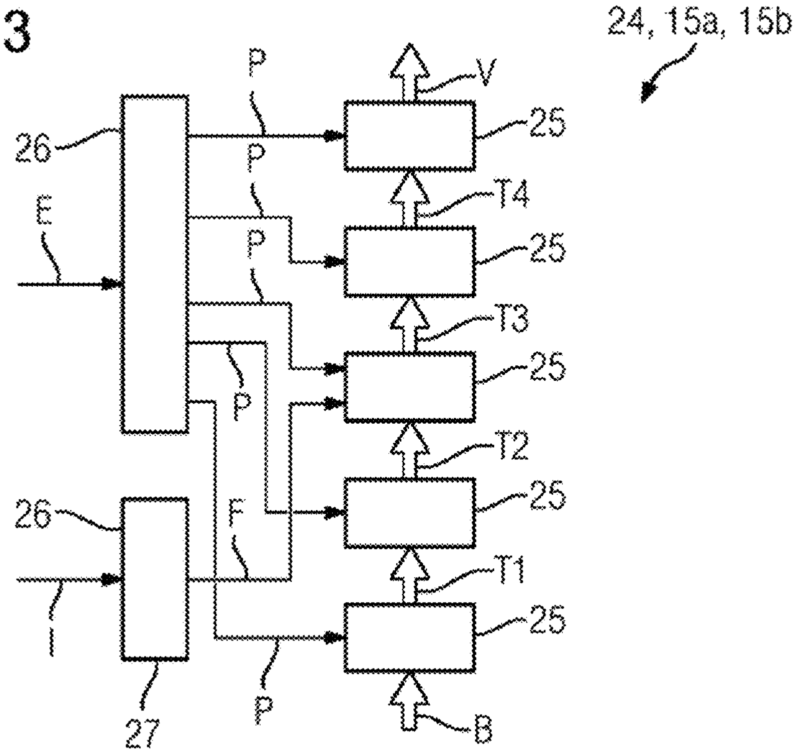
FIG. 3 shows, in a schematic block diagram and in greater detail, one embodiment of image processing pipelines, an event handler, and an assessment management module in standalone operation.

As indicated, diagrammatically and greatly simplified, in FIG. 3, each pipeline 24 includes in each case a plurality of filters 25 that are connected one after the other and each of which performs a particular processing step on the data of the image dataset B in order to generate the view V from the original image dataset B.

In FIG. 3, five filters 25 are illustrated, purely by way of example, and these are, for example, in the order of image processing: a filter 25 for selecting the image extract that is to be displayed of the original image data of the image dataset (including xy centering of the image center and zoom); a filter 25 for extracting the metadata to be displayed from the image dataset and distributing this metadata over the image plane; a filter 25 for selecting stored assessments F that are associated with the image extract and for positioning these assessments on the image plane; a filter 25 for adjusting the data of the image dataset, including the extracted assessments F, to the form factor of the respective device 2; and a filter 25 for combining the selected image data, metadata and assessments F to give the view V.

The functions described in conjunction with the five filters 25 mentioned above may also be distributed over more than five filters 25, or be grouped in a different form. The pipeline 25 may include numerous further filters.

In the course of form factor adjustment, the image data of the image extract to be displayed is adapted to the screen resolution of the associated device 2. During this, the image information is scaled up or down appropriately in order to map the pixels of the image data extract onto a usually different number of screen pixels.

In the course of form factor adjustment, a corresponding metadata image text (e.g., an item of image information containing alphanumeric information) is generated from the extracted metadata, where this image text is generated taking into account the form factor of the associated device 2 in order to provide legibility of the image text.

In the course of form factor adjustment, the extracted assessments F that are distributed over the image plane are converted to a corresponding assessment image (e.g., an item of image information that reproduces the graphical and alphanumeric information). In this partial step, too, the form factor of the associated device 2 is taken into account in order to provide that the assessments are identifiable.

In the course of the combining step, the image text and the assessment image are overlaid on the actual image data. The finished view V thus contains the selected image extract of the image dataset, with a selection of metadata inset therein, and with the assessments F also inset.

Thus, as a result of the pipeline 24, the view V is generated from the underlying image dataset B in a multi-stage process, in that image data, metadata, and assessments F pass through the filters 25 that are connected one after the other and in so doing are successively further processed. During this, the individual filters 25 of the pipeline 24 (with the exception of the last filter 25) each pass partially processed data Ti to T4 on to the respectively downstream filter 25.

The pipeline 24 is constructed such that individual filters 25 may be inserted into the pipeline 24 or removed from the pipeline 24 during the running time of the application 15*a*, 15*b* as a result of user interaction with the GUI 20. For example, a color filter (not explicitly illustrated) for coloring the image data, which is monochrome as standard, is inserted into the pipeline 24 if the user activates the color representation function in the segment 21 by selecting a corresponding menu item. Other filters 25 are inserted into the pipeline 24 or removed from the pipeline 24 automatically, as a function of the type of image dataset B loaded.

Certain properties of at least some of the filters 25 are determined by parameters P that are pre-specified to the filters 25 by an event handler 26.

The event handler 26 determines the parameters P as a function of events E that are supplied and are either generated automatically by the application 15*a*, 15*b* or as a result of user interaction with the GUI 20 (e.g., actuation of the left-hand mouse button in a particular position of the mouse pointer). In the case of the filters 25 mentioned above, the parameters P determine, for example, the xy position of the original image data with respect to which the image extract to be displayed is to be centered, and a zoom factor, options for selecting the metadata, etc. to be displayed, options for presenting the assessments F, specifications of the script size of the metadata and assessments F to be inset, and specifications of whether the metadata image text and/or the assessment image is to be overlaid on the image data.

For management of existing assessments F and for the creation of new assessments F in accordance with corresponding inputs I by the user operating the respective application 15*a*, 15*b*, the applications 15*a*, 15*b* also include a respective assessment management module 27. The assessment management module 27 feeds the existing and newly created assessments F into the pipeline 24.

FIG. 2 shows the applications 15*a* and 15*b* described above in an operating mode in which the segments 21 of the applications 15 of the system 1 operate independently of one another in a manner conventional per se. In this operating mode, designated "standalone operation" below, there is no data exchange between the applications 15*a* and 15*b* and segments 21 thereof. For example, therefore, a joint evaluation of the image dataset B at a plurality of devices 2 is not supported in "standalone operation" by the applications 15*a*, 15*b* either.

In order nonetheless to enable effective joint evaluation of data, the applications 15 of the system 1 are set up such that individual segments 21 of the GUI 20 may be reversibly moved from "standalone operation" into a different operating mode, designated "collaborative operation" below and illustrated by FIGS. 4 and 5.

Figure 4:
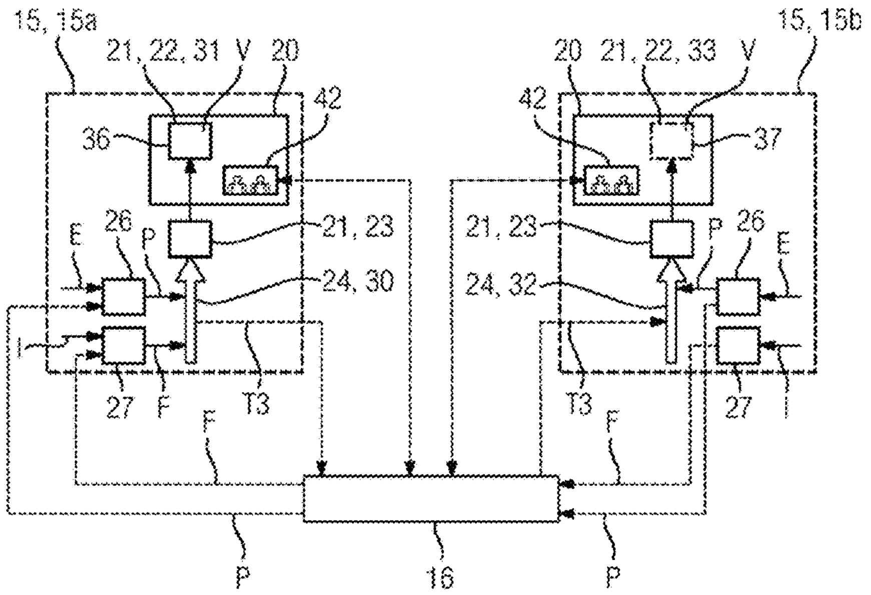
FIG. 4 shows, in an illustration according to FIG. 2, the applications in a collaborative operation.

As shown from FIGS. 4 and 5, collaborative operation is characterized in that the pipelines 24 of two or more segments 21 of different applications 15*a*, 15*b* (which are usefully implemented on different devices 2) are coupled to one another, in that; according to the illustration from FIG. 4, partially processed data T3 is decoupled from the pipeline 24 of the segment 21 of a first application 15 (according to FIG. 4, by way of example, application 15*a*) and coupled to the pipeline 24 of the segment 21 of at least one second application 15 (according to FIG. 4, by way of example, application 15*b*).

In the context of the connotation mentioned above, the pipeline 24 of the application 15*a* and the associated segment 21 are thus operated as the presenter pipeline 30 and the presenter segment 31. The pipeline 24 of the application 15*b* and the associated segment 21 are by contrast operated as the observer pipeline 32 and the observer segment 33.

As shown by FIG. 5, in one embodiment, coupling of the pipelines 24 is achieved in that a respective coupling filter 34 and 35 are connected to the presenter pipeline 30 and the observer pipeline 32, respectively. In this case, the coupling filter 34 decouples the data T3 from the presenter pipeline 30 and transmits this data T3 to the application 15*b*. At the application 15*b*, the coupling module 35 couples the data T3 into the observer pipeline 32 at the same point in the processing sequence.

The coupling filter 34 also outputs partially processed data T3' to the next filter 25 within the presenter pipeline 30. The data T3' is, for example, substantially the same as the decoupled data T3. However, in one embodiment, the data T3' differs from the data T3 with respect to a mark 36 that is added by the coupling module 34 (e.g., in the form of a frame of a particular color (red)), which is displayed as part of the view V in the presenter segment 31 and thus visibly labels the presenter segment 31 as such (FIG. 4).

The coupling filter 35 replaces the data that is processed in the upstream filters 25 of the observer pipeline 32 with the data T3 that is coupled in. The data T3 from the presenter pipeline 30 thus takes over the observer pipeline 32. The coupling filter 35 also adds an additional mark 37 to the data T3 in the embodiment and passes correspondingly modified data T3' on to the downstream filter 25. This mark 37 (FIG. 4) may be generated in the form of a frame of a different color (e.g., yellow), which is displayed as part of the view V in the observer segment 33 and thus visibly labels the observer segment 33 as such.

The coupling filters 34 and 35 are inserted into the presenter pipeline 30 and the observer pipeline 32, respectively, such that all the medically relevant processing steps (e.g., selection of the image extract to be assessed, selection of the metadata to be displayed, selection of the assessments F to be displayed, where appropriate re-coloring of the image data, etc.) are performed only in the presenter pipeline 30 before the data T3 is decoupled. By contrast, form factor adjustment is performed after the data T3 is decoupled and thus takes place in both the presenter pipeline 30 and the observer pipeline 32, separately and independently of one another. Parameters P that are adjusted in each case to the form factor of the associated device 2 are predetermined for the filter 25 carrying out the form factor adjustment in the presenter pipeline 30 and in the observer pipeline 32.

The combination of selected image data with metadata and assessments F (e.g., the overlaying of the image data with metadata image text and an assessment image) also takes place in both the presenter pipeline 30 and the observer pipeline 32, separately and independently of one another. Image data, metadata, and assessments F are thus decoupled from the presenter pipeline 30 and coupled to the observer pipeline 32 as mutually separated constituent parts of the partially processed data T3, separately and independently of one another.

As a result of this process, the views V that are displayed in the presenter segment 31 and the observer segment 33 always contain the same medical image information, where this image information is in each case presented in a quality optimized for the respective device 2.

In collaborative operation of the applications 15*a* and 15*b*, assessments F that are generated by the assessment management module 27 of the application 15*b* based on inputs I by the user operating this application 15*b* ("observer") are not, as in standalone operation of the application 15*b*, fed into the observer pipeline 32. Rather, these assessments F that are generated at the observer end are transmitted to the application 15*a* and managed by the assessment management module 27 there and are fed into the presenter pipeline 30. As a result, the assessments F generated at the observer end are visible both in the presenter segment 31 and in the observer segment 33.

Only some of the parameters P that are generated by the event handler 26 of the application 15*b* based on events E occurring at the observer end are fed into the observer pipeline 32. Another part of these parameters P is transmitted to the application 15*a* and fed into the presenter pipeline 30 by the event handler 26 there. As indicated in FIG. 5, during this, for example, only the parameters P that relate to the filters 25 upstream of the coupling filters 34 and 35 are transmitted to the application 15*a*. In the example described above, therefore, parameters P that are generated at the observer end and relate to medically relevant image manipulation steps such as selection of the image extract, selection of the metadata, and selection of the assessments F are transmitted to the application 15*a* and fed into the presenter pipeline 30. As a result of this, the effects on the image manipulation process that are caused thereby are visible both in the presenter segment 31 and in the observer segment 33. In this way, the observer may move or enlarge/reduce the image extract presented in the view V in a manner visible to all the users concerned. By contrast, all the parameters P generated at the observer end and relating to the filters 25 downstream of the coupling filters 34 and 35 are fed only into the observer pipeline 32 and thus also only affect the view V displayed in the associated observer segment 33.

As indicated in FIG. 5, transmission of the assessments F generated at the observer end and the parameters P generated at the observer end to the application 15*a* is performed by withdrawable modules 38, 39, 40 and 41 that are coupled in collaborative operation (e.g., in the manner of plug-ins) to the assessment management module 27 at the observer end, the assessment management module 27 at the presenter end, the event handler 26 at the observer end, and the event handler 26 at the presenter end, respectively.

In an alternative embodiment of the system 1, separate withdrawable modules 38, 39, 40 and 41 are not provided. Instead, the function of these withdrawable modules 38-41 is implemented as a fixed (non-separable) constituent, which may be activated and deactivated during the running time of the applications 15*a*, 15*b*, of the assessment management modules 27 and event handlers 26 of the applications 15*a*, 15*b*.

Unlike the process described above, in another embodiment of the system 1 and the method performed therewith, instead of assessments F and parameters P generated at the observer end, the underlying inputs I and events E of the second application 15*b* are transmitted directly to the first application 15*a*. In this case, assessments F and parameters P are derived from the transmitted inputs I and events E at the presenter end, by the application 15*a*.

Each segment 21 of the applications 15*a*, 15*b* may be switched reversibly between standalone operation, according to FIGS. 2, 3, and collaborative operation, according to FIGS. 4, 5, by the respective user by interaction with the GUI 20. For this purpose, an operating element that is designated below as the collaboration pilot 42 (FIG. 4) is displayed to the user by the respective application 15*a*, 15*b*, as a constituent of the GUI 20 (e.g., all the time or on activation by the user).

In this collaboration pilot 42, which is presented by way of example as a window or frame within the respective GUI 20, the identities of the users who have declared their willingness to take part in a collaborative session at a common point in time by interaction with the GUI 20 are displayed. In this context, any collaborative session is characterized by coupling a presentation pipeline 30 to one or more observer pipelines 32 of other applications 15 and thus by an image dataset B that is to be evaluated jointly. With respect to any collaborative session, one of the users concerned may be identified as the presenter in the collaboration pilot 42 by interaction with the GUI 20. The further user or users who has/have declared their willingness to take part in the collaborative session are identified as observers in the collaboration pilot 42.

The user of the application 15*a* who is identified, for example, as the presenter may, by interaction with the GUI 20, mark the segment 21 there (or any of, where appropriate, a plurality of segments displayed in the GUI 20) as the presenter segment 31 by dragging an icon representing himself or herself in the GUI 20 into the desired segment 21. On detecting this user interaction, the application 15*a* switches the segment 21 concerned from standalone operation to collaborative operation, and activates the associated pipeline 24 as the presenter pipeline 30 by attaching the coupling filter 34 to the pipeline 24, according to FIG. 5, and coupling the withdrawable modules 39 and 41 to the assessment management module 27 and the event handler 26, respectively.

Similarly, the user of the application 15*b*, who is identified, for example, as the observer, may, by interaction with the GUI 20, mark the segment 21 there (or any of, where appropriate, a plurality of segments displayed in the GUI 20) as the observer segment 33 by dragging an icon representing himself or herself in the GUI 20 into the desired segment 21. On detecting this user interaction, the application 15*b* also switches the segment 21 concerned from standalone operation to collaborative operation, and activates the associated pipeline 24 as the observer pipeline 32 by attaching the coupling filter 35 to the pipeline 24, according to FIG. 5, and coupling the withdrawable modules 38 and 40 to the assessment management module 27 and the event handler 26 respectively.

Although the system 1 may, within the scope of one or more of the present embodiments, be constructed such that the applications 15*a*, 15*b* exchange data directly (e.g., peer to peer; the partially processed data T3 and assessments F and parameters P that are generated at the observer end), in an embodiment of the system 1, in collaborative operation, each of the applications 15*a*, 15*b* communicates in collaborative operation only with the central collaboration unit 16 that brings about data exchange between the applications 15*a*, 15*b*. In this arrangement, the central collaboration unit 16 also coordinates the collaboration pilot 42 of the applications 15*a*, 15*b*.

In one embodiment of the system 1, each of the applications 15 is constructed for holding a plurality of collaborative sessions simultaneously. In other words, the applications 15 are set up such that, at the choice of the user, one or more segments 21 of the respective GUI 20 may be operated in collaborative operation simultaneously, but within the scope of different collaborative sessions. In an optional embodiment of the system 1, the applications 15 are constructed such that, for each application 15, only a single segment 21 may be operated as the presenter segment 31 at one time.

In one embodiment, in collaborative operation, not only are the partially processed data T3 of the image dataset B and the assessments F and parameters P exchanged between the applications 15*a*, 15*b* concerned, but also sound signals (e.g., captured speech) and optionally video signals from any cameras present on the devices 2 concerned. The sound and video transmission between the applications 15*a*, 15*b* is in this case also may be brought about by way of the central collaboration unit 16.

Figure 6:
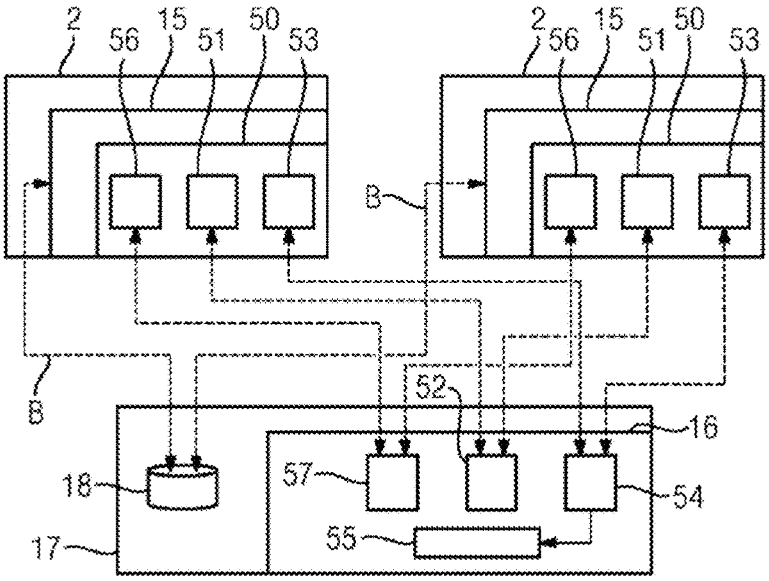
FIG. 6 shows, in a greatly simplified diagram, one embodiment of the structure of the components that enable collaboration between the applications.

In FIG. 6, the components of the system 1 that are involved in realizing the collaborative operation are once again illustrated, in an overview.

FIG. 6 shows that a local collaboration unit 50 that combines the functions and components required for collaboration and communicates with the central collaboration unit 16 is associated with each application 15. The local collaboration unit 50 that is associated with an application 15 thus includes, for example, the coupling filters 34, 35, the withdrawable modules 38-41, and the collaboration pilot 42. As already indicated above, the local collaboration unit 50 may be constructed as separate modules that, for example in the manner of plug-ins, may be coupled to the respectively associated application 15 during running time. In an alternative embodiment, the local collaboration units 50 are implemented as a fixed constituent of the respectively associated application 15*a*, 15*b*.

According to FIG. 6, each local collaboration unit 50 contains a presenter channel 51, by way of which individual segments 21 of the associated application 15 are accorded a respective role as presenter segment 31 or observer segment 33. This presenter channel 51, which, for example, also controls the collaboration pilot 42, communicates with a module of the central collaboration unit 16 that is designated the presentation manager 52. In this context, the presentation manager 52 coordinates the roles of the segments 21 that are concerned, in the collaborative sessions that in each case involve more than one application.

Each local collaboration unit 50 contains an event channel 53, via which the events relevant to the collaboration are signaled between the applications 15. These events include, for example, the provision of partially processed data T3 through the presenter pipeline 30, and the generation of new assessments F and parameters P at the observer end. This event channel 53, which cooperates, for example, with withdrawable modules 38-41 according to FIG. 5, communicates with a corresponding module of the central collaboration unit 16 that is designated the event manager 54. The event manager 54 manages and passes on the events that are fed to the event manager 54 in a manner involving more than one application.

The exchange of the data T3, assessments F and parameters P that are connected with these events, is brought about via a module of the central collaboration unit 16 that is designated the data exchange manager 55. The data exchange manager 55 handles the data for exchange independently of the respective data type, and in this sense, has no format.

Each local collaboration unit 50 contains an audio channel 56 via which sound signals (and where appropriate video signals) that are captured in the course of the collaboration are exchanged. This audio channel 56 communicates with a corresponding module of the central collaboration unit 16 that is designated the audio manager 57, where the audio manager 57 manages and passes on the sound signals (and where appropriate video signals) that are fed to the audio manager 57.

The invention is made clear by the exemplary embodiments described above, but nonetheless is not restricted to these exemplary embodiments. Rather, numerous further embodiments of the invention may be derived from the claims and the description above. For example, within the scope of the claims, individual features of the exemplary embodiments may be omitted, combined in a different way, or replaced by further features without departing from the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for joint evaluation of a medical image dataset on a first data processing device and at least one second data processing device that is connected to the first data processing device via a data transmission network, the method comprising:

performing a first application in the first data processing device and performing a second application in the at least one second data processing device, the first application and the second application being software applications for displaying, processing, or displaying and processing the medical image dataset; and generating a view of the medical image dataset, the generating comprising combining image data of the medical image dataset with data of at least one further data type, the at least one further data type including metadata, assessments, or metadata and assessments, wherein each of the first application and the second application has a respective graphical user interface having at least one segment for display of the view of the medical image dataset, wherein the view is derived from the medical image dataset by an image processing pipeline that is associated with the respective segment in a multi-stage processing process, wherein the at least one segment of the first application is operated as a presenter segment in that partially processed data of the medical image dataset is decoupled from the image processing pipeline of the presenter segment and is transferred to the second application, wherein the at least one segment of the second application is operated as an observer segment in that the transferred partially processed data of the medical image dataset is coupled to the image processing pipeline of the observer segment for preparing the view, and wherein the image data and the data of the at least one further data type are decoupled separately from one another from the image processing pipeline of the presenter segment and coupled to the image processing pipeline of the observer segment and are combined there to give the view.

2. The method of claim 1, wherein the partially processed data of the medical image dataset is decoupled from the image processing pipeline of the presenter segment before form factor adjustment has been performed, and is coupled to the image processing pipeline of the observer segment before form factor adjustment.

3. The method of claim 2, further comprising generating, by user interaction with the user interface of the second application, an assessment in the observer segment, wherein the assessment is transferred to the first application and at the first application is fed into the image processing pipeline of the presenter segment.

4. The method of claim 2, wherein one segment of a plurality of segments of the user interface of the first application is selected as the presenter segment by user interaction with the user interface of the first application, wherein one segment of a plurality of segments of the user interface of the second application is selected as the observer segment by user interaction with the user interface of the second application.

5. The method of claim 1, further comprising generating, by user interaction with the user interface of the second application, an assessment in the observer segment, wherein the assessment is transferred to the first application and at the first application is fed into the image processing pipeline of the presenter segment.

6. The method of claim 1, wherein one segment of a plurality of segments of the user interface of the first application is selected as the presenter segment by user interaction with the user interface of the first application, wherein one segment of a plurality of segments of the user interface of the second application is selected as the observer segment by user interaction with the user interface of the second application.

7. The method of claim 1, further comprising generating respective graphical user interfaces for each of the first application and the second application.

8. A system for joint evaluation of a medical image dataset, the system comprising:

at least a first data processor and at least a second data processor; and a data transmission network via which the first data processor and the second data processor are connected, wherein a first application is implemented in the first data processor, and a second application is implemented in the second data processor, the first application and the second application being software applications for displaying, processing, or displaying and processing the medical image dataset, wherein each application of the first application and the second application has a respective graphical user interface having at least one segment for display of a view of the medical image dataset, wherein an image processing pipeline for generating the view from the medical image dataset is associated with each segment in a multi-stage processing process, wherein the first application is configured to decouple partially processed data of the medical image dataset from the image processing pipeline of the associated segment and to transfer the decoupled partially processed data to the second application in order to operate the associated segment as a presenter segment, wherein the second application is configured to receive the transferred partially processed data of the medical image dataset and to couple the transferred partially processed data to the image processing pipeline of the associated segment for preparing the view in order thus to operate this segment as an observer segment, wherein the image processing pipeline of the presenter segment and the image processing pipeline of the observer segment are each configured to generate the view, the generation of the view comprising a combination of image data of the medical image dataset with data of at least one further data type, the at least one further data type including metadata, assessments, or metadata and assessments, wherein the first application is configured to decouple the image data and the data of the at least one further data type separately from one another from the image processing pipeline of the presenter segment, and wherein the second application is configured to couple the image data and the data of the at least one further data type separately from one another to the image processing pipeline of the observer segment and to combine the image data and the data of the at least one further data type there to give the view.

9. The system of claim 8, wherein the first application is configured to decouple the partially processed data of the medical image dataset from the image processing pipeline of the presenter segment before form factor adjustment, and wherein the second application is configured to couple the partially processed data of the medical image dataset to the image processing pipeline of the observer segment before form factor adjustment.

10. The system of claim 8, wherein the second application is configured such that, by user interaction with the associated user interface, an assessment is generateable in the observer segment, wherein the second application is configured to transfer the assessment to the first application, and wherein the first application is configured to feed the assessment into the image processing pipeline of the presenter segment.

11. The system of claim 8, wherein the user interface of the first application includes a plurality of segments, each segment of the plurality of segments of the user interface of the first application being selectable as the presenter segment by user interaction with the user interface of the first application, the user interface of the second application includes a plurality of segments, each segment of the plurality of segments of the user interface of the second application being selectable as the observer segment by user interaction with this user interface, or a combination thereof.

12. The system of claim 8, further comprising a central collaboration unit configured to bring about the data transfer between the first application and the second application.

13. The system of claim 12, wherein the central collaboration unit is implemented in a cloud.

* * * * *